(12) United States Patent
Neftin (10) Patent No.: US 9,066,544 B1
(45) Date of Patent: Jun. 30, 2015

(54) PROTECTIVE KNEE PADS FOR TODDLERS AND CHILDREN

(71) Applicant: Jean Neftin, Brooklyn, NY (US)

(72) Inventor: Jean Neftin, Brooklyn, NY (US)

( * ) Notice: Subject to any disclaimer, the term of this patent is extended or adjusted under 35 U.S.C. 154(b) by 0 days.

(21) Appl. No.: 14/011,127

(22) Filed: Aug. 27, 2013

(51) Int. Cl.
*A41B 13/00* (2006.01)

(52) U.S. Cl.
CPC ........................... *A41B 13/00* (2013.01)

(58) Field of Classification Search
CPC ................... A41D 11/00; A41D 13/065
USPC ............................................ 2/24, 16
See application file for complete search history.

(56) References Cited

U.S. PATENT DOCUMENTS

| | | | | |
|---|---|---|---|---|
| 1,969,527 | A | * | 8/1934 | Schnellbacher ............. 2/24 |
| 2,650,362 | A | * | 9/1953 | Musgrave ................. 2/24 |
| 2,794,982 | A | * | 6/1957 | Kay ...................... 2/24 |
| 3,389,582 | A | * | 6/1968 | Alexander ............... 66/192 |
| 3,411,222 | A | * | 11/1968 | Williams ................ 434/255 |
| 4,845,778 | A | * | 7/1989 | Peterson .................. 2/24 |
| 4,879,765 | A | * | 11/1989 | Bailie et al. ............. 2/24 |
| D312,147 | S | * | 11/1990 | Lapin .................. D29/121.1 |
| D335,000 | S | * | 4/1993 | Johnson ............... D29/121.1 |
| D344,609 | S | * | 2/1994 | Lapin .................. D29/121.1 |
| 5,592,689 | A | * | 1/1997 | Matthews ................ 2/23 |
| 5,794,275 | A | * | 8/1998 | Donzis .................. 2/455 |
| D431,883 | S | * | 10/2000 | Obadiaru et al. ...... D29/121.1 |
| 7,273,464 | B2 | * | 9/2007 | Reinhardt ................ 602/26 |
| D568,546 | S | * | 5/2008 | Mehrabani ............. D29/117.2 |
| 7,987,518 | B2 | * | 8/2011 | Calderwood ............... 2/24 |
| 2006/0117451 | A1 | * | 6/2006 | Sciortino ................. 2/23 |
| 2006/0179545 | A1 | * | 8/2006 | Arensdorf et al. .......... 2/227 |
| 2008/0115248 | A1 | * | 5/2008 | Meadows ................. 2/22 |
| 2009/0048550 | A1 | * | 2/2009 | Feeley et al. ............ 602/26 |
| 2010/0154094 | A1 | * | 6/2010 | Calderwood .............. 2/24 |
| 2013/0111641 | A1 | * | 5/2013 | Colanto et al. ........... 2/16 |

* cited by examiner

*Primary Examiner* — Richale Quinn
(74) *Attorney, Agent, or Firm* — Mark R. Malek; Daniel C. Pierron; Widerman Malek, PL (57) ABSTRACT

A knee pad includes a double layer elastic fabric tube which is proportioned to cover the knee region of a child and a pattern of rubber-like miniature pads located on the outer surface of the fabric tube. The elastic fabric tube includes an outer layer and an inner layer. The inner surfaces of both of the layers include cloth loops which are disposed in a facing relationship with each other allowing the outer and inner layers to slide relative to one another.

16 Claims, 7 Drawing Sheets

PROTECTIVE KNEE PADS FOR TODDLERS AND CHILDREN

FIELD OF THE INVENTION

The present invention generally relates to the field of protective equipment and more particularly to protective knee pads for toddlers and children.

BACKGROUND OF THE INVENTION

When toddlers first learn to crawl it is necessary to protect their knees from redness and irritation. Additionally, their knees need to be protected from abrasions during forward falls during the first steps and active play both indoors and outdoors. As a result, a solution is required that will accommodate the growth of the child and will offer protection as the child progresses from crawling to walking.

The prior art includes several examples of knee pads for children included among which are the following:

U.S. Pat. No. 6,332,224 to Walker (2001) discloses knee pads that are incorporated into socks or sock bands which offer protection during crawling. These knee pads are prohibitively expensive to manufacture. They do not provide enough breathability in a warm environment since they cover the most of the leg. Additionally, they do not offer any traction on a bare floor or wood due to the fact that the knee pad is internal and the textile surface of the sock offers little or no traction. As a result, the knee pads according to Walker cannot be considered to be effective.

U.S. Patent 2009/0048550 to Feeley (2009) shows knee pads that solve some but not all of the issues of the Walker device. The Feely device protects the child's knee through the use of a frontal facing silicone pad. It becomes ineffective as soon as the silicone pads slide sideways during crawling and as a result exposes the knee to the crawling surface with nothing to absorb the impact.

U.S. Pat. No. Des 417,037 to Bitter (1999) discloses knee pads that are secured by a strap with a Velcro fastener. This device will tend to irritate the child's skin during the bending and unbending of the leg and this device will tend to constrict the child's leg and interfere with normal blood circulation.

While most of the knee pads in the prior art offer some level of protection, they all suffer from a number of disadvantages. The prior art knee pads are too bulky and the frontal facing pad becomes ineffective when knee pads rotate on the child's leg and move sideways. The frontal facing pads frequently need to be adjusted by a parent or guardian to maintain the desired frontal position.

If a protective hard shell is used in a knee pad and the hard shell is too thick it will elevate the child's hips above the elevation of the child's shoulder area and thus put unnecessary stress on the shoulder joints and the lower back thus increasing the chances of shoulder injuries and forward falls on to the child's face.

Despite the developments of the prior art there remains a need for a safe and effective knee pad for toddlers and children. There is no protective gear presently available on the market which is capable of providing a toddler or a child with a lightweight, knee conforming, breathable apparatus which may be comfortably worn on the child's leg around the knee area to reduce the likelihood of painful skin irritation or abrasion.

OBJECTS AND SUMMARY OF THE INVENTION

It is an object of the present invention to provide a knee pad which provides effective protection for the knees of toddlers and children while providing appropriate traction to make crawling easier.

Another object of the present invention is to provide a knee pad for toddlers and children which is not subject to becoming dislodged during use.

Another object of the present invention is to provide a knee pad for toddlers and children which remains effective even during extended use.

Another object of the present invention is to provide a knee pad for toddlers and children which does not elevate the knees and hips of the user while crawling.

Another object of the present invention is to provide a pad for protecting the knee area of the toddler or child which is fabricated from an elastic, knit material and which provides increased traction on bare surfaces during crawling.

Another object of the present invention is to provide a pad for protecting the knee area of a toddler or child which is lightweight, breathable, comfortable, and capable of economic fabrication.

Another object of the instant invention is to provide a method for the efficient manufacture of knee pads for protecting the knee area of a toddler or child.

Yet another object of the present invention is to provide a knee pad for toddlers and children which can be manufactured economically in volume resulting in a relatively low unit cost.

Additional objects and advantages of the present invention will be made clear hereinafter.

In accordance with the present invention, there is provided a knee pad for toddlers and children which includes a double layer elastic fabric tube configured to cover the knee region and a pattern or array of silicone, plastic or rubber based miniature pads or shapes which are disposed over the patella of the child, when utilized. The miniature pads are molded onto or adhered to the surface of the tube by mechanical, thermal, chemical or other means.

In an exemplary primary embodiment of the invention, the knee pad includes a knit or woven elastic fabric tube that is proportioned to cover the knee region of the toddler or child when utilized. The elastic fabric tube includes an outer layer and an inner layer. The inner surfaces of both the inner and outer layers include terry cloth loops disposed against or facing each other. The terry cloth loops can be of variable lengths with a preferred length of between about one (1) mm and about seven (7) mm.

The layers described provide compliance or softness resulting in shock absorption and protection for the child and also allow a degree of relative sliding to occur between the layers during use. This sliding motion between the inner and outer layers prevents the transmission of forces which otherwise would tend to cause abrasion on the child's knees.

The outer and inner layers are formed by folding the ends of a long tube of elastic knit or woven material inwardly and sewing the folded ends together. The miniature pads on the front of the knee pad can have various shapes and can be arranged in a variety of shapes or patterns.

The invention also provides a method of manufacturing a knee pad for a toddler or child comprising: forming an elastic fabric tube that is proportioned to cover the knee region of the toddler or child when utilized. The elastic fabric tube includes an outer layer and inner layer. The inner surfaces of both the inner and outer layers include cotton yarn or other fabric forming terry cloth type loops which are directed in a mutually facing relationship.

A second embodiment of the invention is similar to the primary embodiment described above with the exception that the plurality of pads has been eliminated.

BRIEF DESCRIPTION OF THE DRAWINGS

Additional details of construction of the present invention will be described with reference to the drawings in which.

DETAILED DESCRIPTION OF THE INVENTION

With reference to the drawings, there is shown in FIGS. 1-6 a protective knee pad 10, for toddlers or children which includes a tube-like member 12 which is formed of an elastic knit or woven fabric and, in the primary embodiment of the invention, a plurality of miniature pads 14. The knee pads according to the present invention are used in pairs. which are identical and therefore only a single knee pad 10 will be described.

The tube-like member 12 is a double layered elastic fabric tube configured to cover the knee region of a child. The plurality of miniature pads 14 may be made of silicone, plastic or rubber-material and is disposed over the patella of the child. The miniature pads 14 are attached to the outer surface 16 of the fabric tube 12 using a molding, mechanical, thermal, chemical or other known attachment process.

Figure 2:
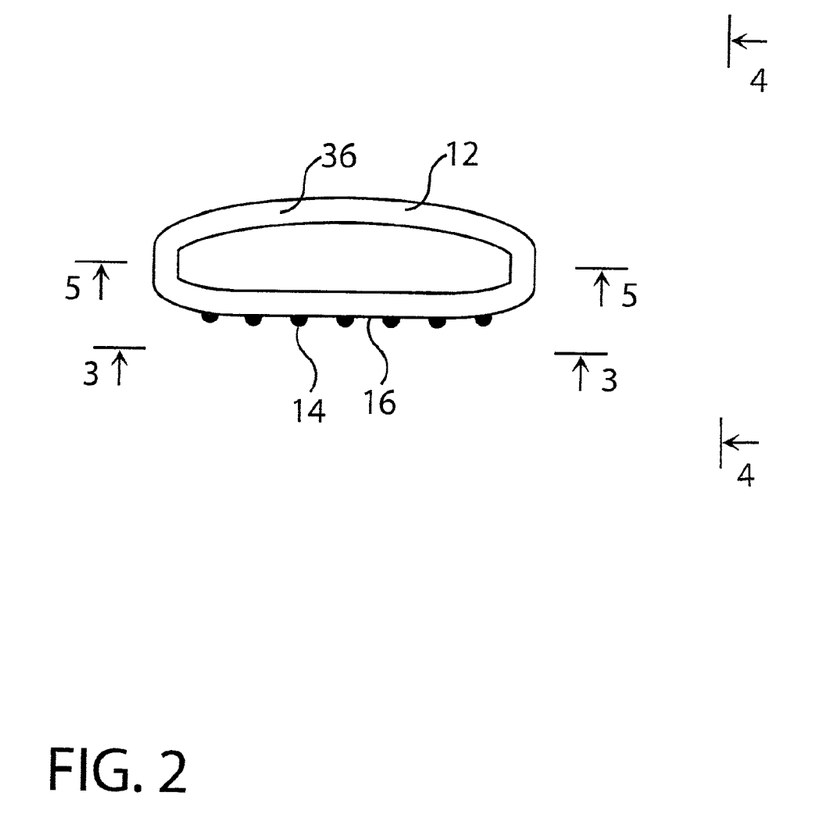
FIG. 2 is a top plan view of the knee pad of FIG. 1.
Figure 3:
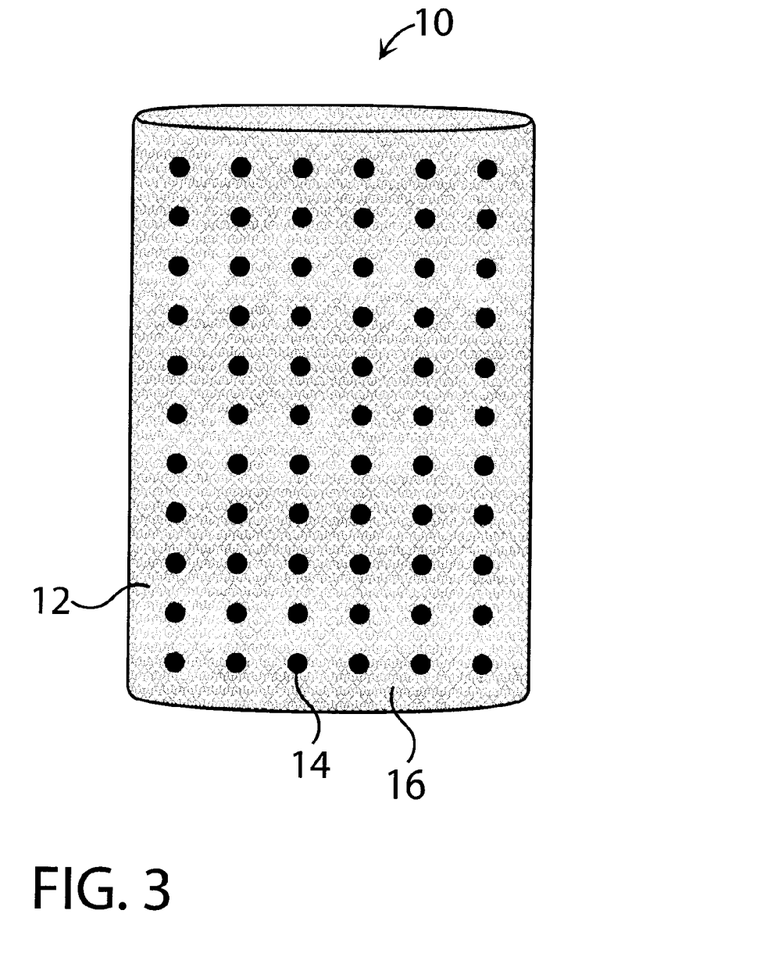
FIG. 3 is a front elevation view of the knee pad of FIG. 1 taken along the line 3-3 of FIG. 2.

The miniature pads 14 may be circular or nearly circular, as illustrated in FIG. 2, or square, rectangular, oval, triangular or irregular in shape. The miniature pads 14 may have a configuration which resembles a human or an animal's body part such as the paw print of a bear or other animal.

Figure 1:
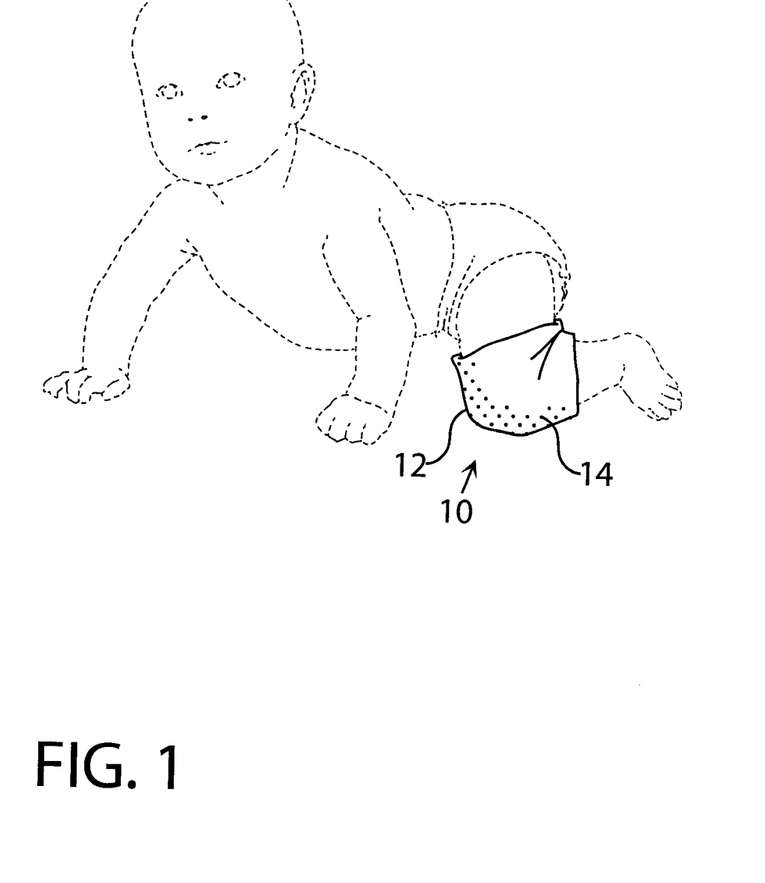
FIG. 1 is an overall perspective view of a knee pad for toddlers and children made in accordance with the present invention with the knee pad shown in use.

The elastic fabric tube 12 is proportioned to cover the knee region of the toddler or child when the knee pad is utilized as is shown in FIG. 1. The elastic fabric tube 12 includes an outer layer 18 and an inner layer 20. The inner surfaces 22, 24 of both of the outer and inner layers 18, 20 include terry cloth-like loops 26 made of cotton, or other fabric. The loops 26 on the outer and inner layers 18, 20 are disposed in a mutually facing relationship. The terry cloth loops 26 can be of variable lengths with a preferred length of between about one (1) mm and about seven (7) mm.

The layers 18, 20 as described provide compliance or softness resulting in shock absorption and protection for the child. The length of the loops 26 has been established through a process of experimentation to provide an optimal desirable degree of softness. In addition, the combination of the optimal length of the loops 26 facilitates a degree of relative sliding to occur between the outer and inner layers 18, 20. This sliding occurs as a result of the relative high degree of traction or friction between the plurality of miniature pads 14 and the floor while the child is crawling and the relatively lower degree of friction between the outer and inner layers 18, 20 which is created as a result of the optimal length of the loops 26.

This sliding action between the outer and inner layers 18, 20 prevents unwanted forces from being transmitted the child's knees which can cause abrasion. As a result, the knee pads 10 according to the present invention provide a highly desirable combination of benefits of softness to reduce the danger of shock and relative sliding motion between the layers 18, 20 to prevent abrasion or irritation of the skin on child's knees.

The construction of the tube member 12 may be accomplished by using a knitting or weaving process. The thread types or yarn types found to be desirable are silk, cotton, linen, rayon, wool, fleece, synthetic, mixed or specialty threads with a denier or gage in the order of 1 to 600. The thread count of the tube member 12 is in the order of 1 to 1000. The thread or yarn used for the fabrication of the tubular member 12 may be silk, cotton, linen, rayon, wool, fleece, synthetic, mixed or specialty threads or other conventional and known materials which are washable and which form a breathable fabric. Mixed and specialty threads are defined as selected combinations of silk, cotton, linen, rayon, wool, fleece, synthetic, mixed or specialty threads or other conventional and known materials which are twisted together or otherwise combined for knitting or weaving.

These parameters have been found to result in the desired combination of elasticity which facilitates the placement of the knee pads 10 on the child's legs, the desired degree of softness with aids in preventing injury and the ability of the layers to slide one relative to another thereby preventing abrasion.

Figure 6:
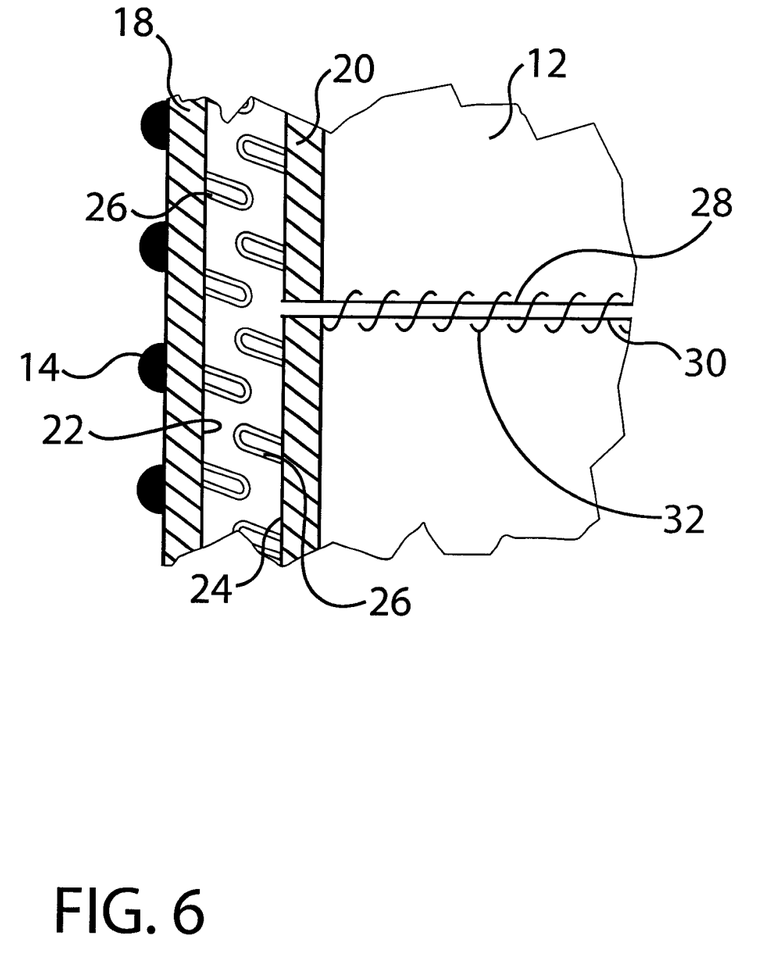
FIG. 6 is a fragmentary cross-sectional view similar to FIG. 5 drawn to an enlarged scale and showing details of construction.
Figure 7:
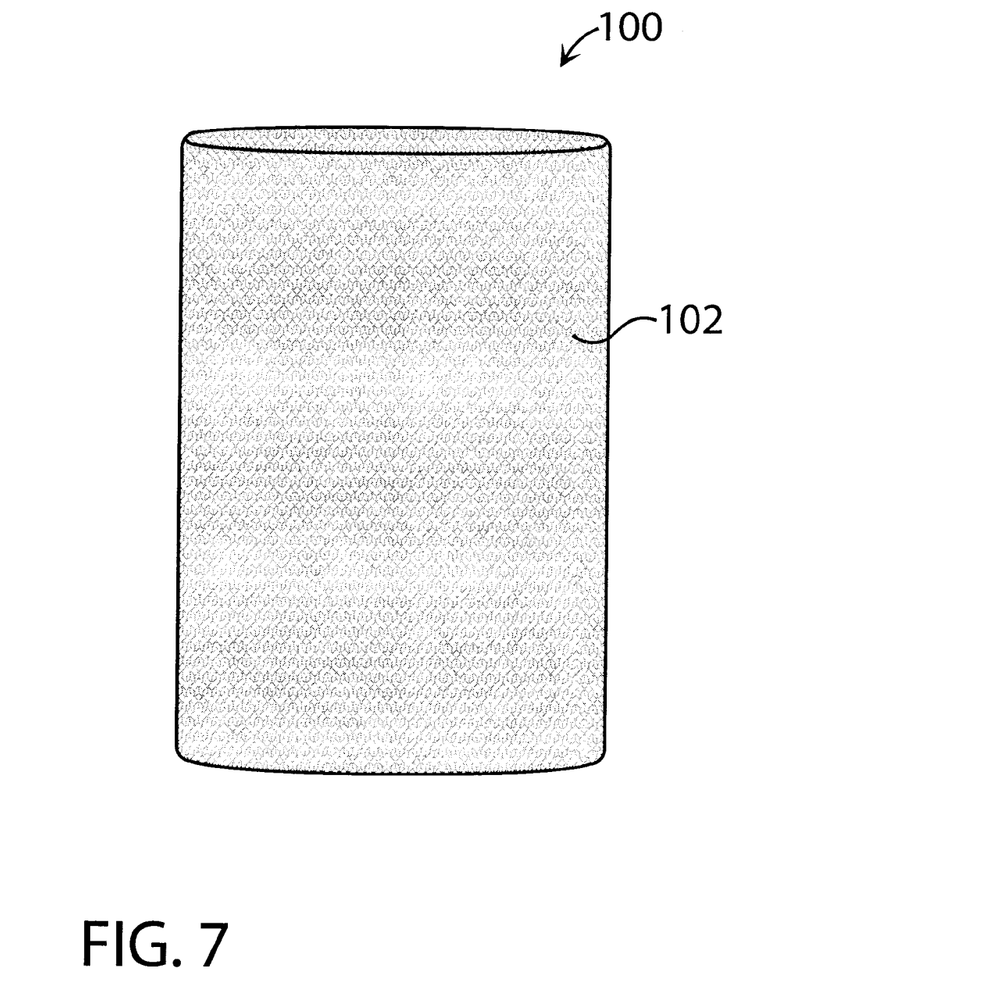
FIG. 7 is a front elevation view of a second embodiment of the invention.

A second embodiment of the invention 100 is shown in FIG. 6 and is identical to the primary embodiment 10 described above with the exception that the plurality of miniature pads 14 has been eliminated from the tube member 102.

The present invention also provides a method of manufacturing a knee pad 10, 100 for a toddler or child, comprising the steps of: forming an elastic fabric tube 12, 102 that is sized to cover the knee region of the toddler or child, folding the ends 28, 30 of the fabric tube inwardly and sewing the ends 28, 30 together.

In the primary embodiment of the invention 10 there is an additional step of attaching a plurality of miniature pads 14 to the outer surface 16 of the elastic fabric tube 12. The step of attaching the plurality of miniature pads 14 to the surface 16 of the outer layer 18 may be accomplished by molding or a mechanical, thermal, chemical or other conventional process.

The present invention thus provides a knee pad 10, 100 for protecting the knee area of child while engaging in both indoor and outdoor activities such as crawling, playing, or the like. The knee pad 10, 100 incorporates an elastic two layered fabric tube 12, 102 configured to cover a knee region of a toddler or a child. The tube 12, 102 has two independent layers that are unconnected internally and thus permit independent sliding between the two layers thereby providing cushioning during forward falls and crawling. In the primary embodiment of the invention the front of the knee pad 10 area includes a plurality of miniature pad-like shapes 14, made out of a rubber-like material, silicone or similar material, that are adhered and/or molded by mechanical, thermal, chemical or other means in order to enhance traction and prevent sliding on such surfaces as linoleum, wood or similar surfaces during crawling and similar activities.

The present invention in the primary embodiment 10 includes a method for the fabrication of protective knee pads which includes the following steps:

Forming a tubular fabric member 12 with the tubular fabric member 12 having an inner surface and an outer surface and with the inner surface having a terry cloth-like surface and having a multiplicity of loop portions 26. The loop portions 26 have a preferred length in the order of one (1) to seven (7) mm in length. The forming step may be accomplished by knitting, weaving or other known conventional techniques.

The ends 28, 30 of the tubular member 12 are then folded inwardly toward the interior 34 of the tubular member 12.

Figure 4:
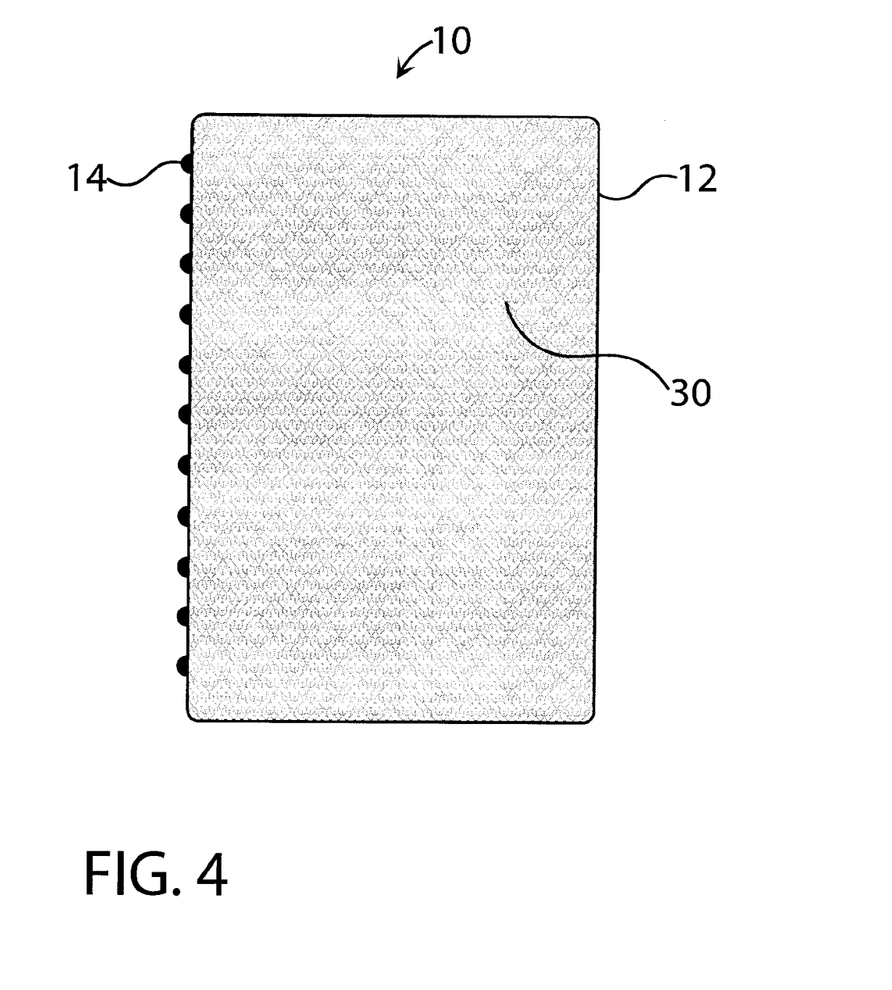
FIG. 4 is a side view taken along the line 4-4 of FIG. 1.
Figure 5:
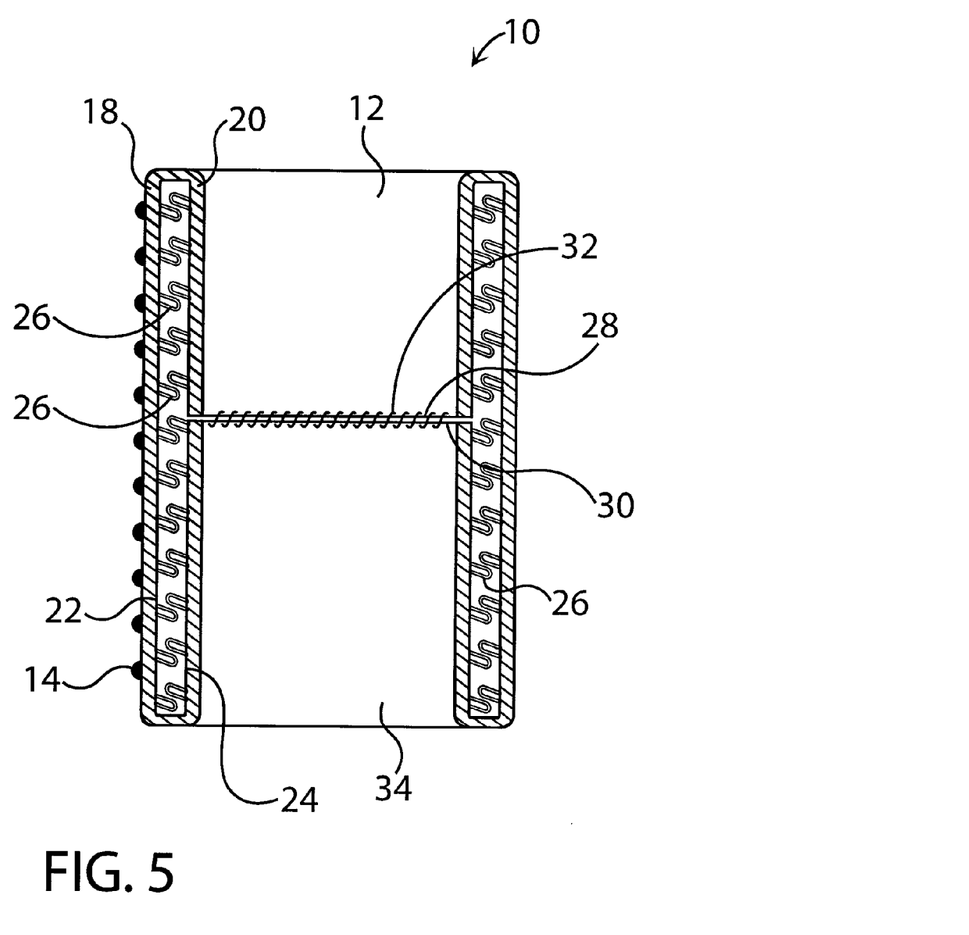
FIG. 5 is a cross-sectional view taken along the line 5-5 of FIG. 2.

The two ends 28, 30 of the tubular member are then joined together by sewing, as illustrated by the stitches 32 in FIGS. 4 and 5, adhesion or other known conventional fabric joining methods thereby forming a double walled or double layered tubular member 12 with the loop portions 26 of the two layers 18, 20 disposed in a facing relationship.

Attaching a plurality of miniature pad members 14 to the outside surface 16 of the tubular member 12. The miniature pad members 14 may be made of silicone, plastic, rubber or rubber-like material. The miniature pads 14 may be attached by molding, printing, heat sealing or other known attachment techniques with the miniature pads forming a regular or a non-regular array.

The present invention in the second embodiment 100 includes a method for the fabrication of protective knee pads which includes the following steps which are similar to the steps of the primary embodiment:

Forming a tubular fabric member with the tubular fabric member having an inner surface and an outer surface and with the inner surface having a terry cloth-like surface and having a multiplicity of loop portions. The loop portions have a preferred length in the order of one (1) to seven (7) mm in length. The forming step may be accomplished by knitting, weaving or other known conventional techniques.

The ends of the tubular member are then folded inwardly toward the interior of the tubular member.

The two ends of the tubular member are then joined together by sewing, adhesion or other known conventional fabric joining methods thereby forming a double walled or double layered tubular member with the loop portions of the two layers disposed in a facing relationship.

The foregoing specific embodiments of the present invention as set fort in the specification are for illustrative purposes only. Various deviations and modifications may be made within the spirit and scope of the invention without departing from a main theme thereof.

What is claimed is:

1. Protective knee pad comprising: an elastic tubular fabric member having a first tubular layer, and a second tubular layer with said first layer disposed outwardly relative to said second layer and whereby said first layer and said second layer having facing surfaces and are separated by a space, further comprising: a plurality of loop portions formed on each of said facing surfaces.

2. The protective knee pad as claimed in claim 1 with said first layer comprising: an outer surface and further comprising: a plurality of miniature pads disposed on said outer surface of said first layer.

3. The protective knee pad as claimed in claim 2 wherein said miniature pads form a regular array.

4. The protective knee pad as claimed in claim 2 wherein said plurality of miniature pads each comprise: a rubber-like material.

5. The protective knee pad as claimed in claim 2 wherein said plurality of miniature pads each comprise: a silicone material.

6. The protective knee pad as claimed in claim 2 wherein said plurality of miniature pads each comprise: a plastic material.

7. The protective knee pad as claimed in claim 1 wherein said miniature pads form a non-regular pattern.

8. The protective knee pad as claimed in claim 1 wherein said elastic tubular fabric member comprises: a knitted fabric.

9. The protective knee pad as claimed in claim 1 wherein said elastic tubular fabric member comprises: a woven fabric.

10. The protective knee pad as claimed in claim 1 wherein said elastic tubular fabric member comprises: a cotton fabric.

11. The protective knee pad as claimed in claim 1 wherein said loop portions have a preferred length ranging from one (1) to seven (7) mm.

12. The protective knee pad as claimed in claim 1 wherein said elastic tubular fabric member comprises: a fabric formed of a material chosen from a group consisting of silk, linen, rayon, wool, fleece, synthetic, mixed or specialty threads.

13. The protective knee pad as claimed in claim 1 wherein said elastic tubular fabric member comprises: a fabric formed of a thread having a denier in the range of 1 to 600.

14. The protective knee pad as claimed in claim 1 wherein said elastic tubular fabric member comprises: a fabric having a thread count in the range of 1 to 1000.

15. Protective knee pad comprising: an elastic tubular fabric member comprising: an outer surface and an inner surface with said elastic tubular layer having a pair of opposite ends and with said pair of opposite ends each folded inwardly toward said inner surface and with said opposite ends joined one to another thereby forming a dual layer tube with said dual layer tube having facing internal surfaces, that are separated by a space, and a plurality of loop portions formed on each of said facing internal surfaces; wherein the outer surface overlies the inner surface relative to a longitudinal axis of the protective knee pad.

16. The protective knee pad as claimed in claim 15 wherein said plurality of loop portions form terry cloth loops.

* * * * *